(12) United States Patent
Forstein et al.

(10) Patent No.: US 12,357,401 B2
(45) Date of Patent: Jul. 15, 2025

(54) SYSTEM AND METHOD FOR OPERATING A SURGICAL ROBOT

(71) Applicant: CUREXO, INC., Seoul (KR)

(72) Inventors: Micah Forstein, Freemont, CA (US); Joel Zuhars, Freemont, CA (US)

(73) Assignee: CUREXO, INC., Seoul (KR)

( * ) Notice: Subject to any disclaimer, the term of this patent is extended or adjusted under 35 U.S.C. 154(b) by 727 days.

(21) Appl. No.: 16/797,091

(22) Filed: Feb. 21, 2020

(65) Prior Publication Data

US 2020/0268461 A1 Aug. 27, 2020

Related U.S. Application Data

(60) Provisional application No. 62/809,301, filed on Feb. 22, 2019.

(51) Int. Cl.
| | | |
|---|---|---|
| *A61B 34/30* | (2016.01) | |
| *A61B 17/16* | (2006.01) | |
| *A61B 17/00* | (2006.01) | |
| *A61B 17/56* | (2006.01) | |
| *A61B 34/00* | (2016.01) | |
| *A61B 34/20* | (2016.01) | |
| *A61B 34/37* | (2016.01) | |
| *A61B 90/00* | (2016.01) | |

(52) U.S. Cl.
CPC .......... *A61B 34/30* (2016.02); *A61B 17/1626* (2013.01); *A61B 2017/00115* (2013.01); *A61B 2017/00694* (2013.01); *A61B 17/16* (2013.01); *A61B 2017/564* (2013.01); *A61B 2034/2055* (2016.02); *A61B 2034/2068* (2016.02); *A61B 34/37* (2016.02); *A61B 34/70* (2016.02); *A61B 2090/065* (2016.02); *A61B 2090/363* (2016.02); *A61B 2562/0261* (2013.01)

(58) Field of Classification Search
CPC ..... A61B 17/1626; A61B 34/76; A61B 34/77; A61B 2090/064; A61B 2090/065
See application file for complete search history.

(56) References Cited

U.S. PATENT DOCUMENTS

| | | |
|---|---|---|
| 5,086,401 A | 2/1992 | Glassman et al. |
| 6,033,415 A | 3/2000 | Mittelstadt et al. |
| 6,061,644 A | 5/2000 | Leis |
| 6,322,567 B1 | 11/2001 | Mittelstadt et al. |
| 7,206,626 B2 | 4/2007 | Quaid, III |
| 8,010,177 B2 | 8/2011 | Csavoy et al. |
| 8,287,522 B2 | 10/2012 | Moses et al. |
| 8,876,830 B2 | 11/2014 | Hodorek et al. |
| 8,961,536 B2 | 2/2015 | Nikou et al. |

(Continued)

*Primary Examiner* — Anu Ramana
(74) *Attorney, Agent, or Firm* — Bridgeway IP Law Group, PLLC; Jihun Kim

(57) ABSTRACT

A method for improved robotic cutting, the method comprising: determining at least one of cutting force data and bone motion data during robotic cutting; determining when at least one of the cutting force data and bone motion data exceeds a predetermined parameter; and when it is determined that at least one of the cutting force data and the bone motion data exceeds the predetermined parameter, providing the user with an indication of the same and pausing the robotic cutting so as to enable the user to mitigate the cause of at least one of the cutting force data and the bone motion data exceeding the predetermined parameter.

20 Claims, 6 Drawing Sheets

(56) References Cited

U.S. PATENT DOCUMENTS

| | | | | |
|---|---|---|---|---|
| 9,084,613 B2* | 7/2015 | Qutub | ................ | A61B 34/10 |
| 10,052,165 B2* | 8/2018 | Cohen | ................ | A61B 34/30 |
| 11,033,344 B2* | 6/2021 | Overmyer | ............ | A61B 90/37 |
| 2013/0060278 A1 | 3/2013 | Bozung et al. | | |
| 2017/0245945 A1 | 8/2017 | Zuhars et al. | | |
| 2018/0344409 A1 | 12/2018 | Bonny et al. | | |
| 2021/0307833 A1* | 10/2021 | Farley | ................ | A61B 90/98 |

* cited by examiner

SYSTEM AND METHOD FOR OPERATING A SURGICAL ROBOT

REFERENCE TO PENDING PRIOR PATENT APPLICATION

This patent application claims benefit of prior U.S. Provisional Patent Application Ser. No. 62/809,301, filed Feb. 22, 2019 by THINK Surgical, Inc. and Micah Forstein et al. for USE OF BONE MOTION AND CUTTING FORCE FEEDBACK DURING ROBOTIC SURGERY TO IMPROVE ROBOTIC CUTTING, which patent application is hereby incorporated herein by reference.

TECHNICAL FIELD

The present invention generally relates to the field of robotic orthopedic surgery, and more particularly to a system and method which use bone motion and cutting force feedback during robotic surgery to improve robotic cutting.

BACKGROUND

Throughout a lifetime, bones and joints become damaged and worn through normal use, disease, and traumatic events. Arthritis is a leading cause of joint damage, which can cause cartilage degradation, pain, swelling, stiffness, and bone loss over time. If the pain associated with the dysfunctional joint is not alleviated by less-invasive therapies, the joint may need to be replaced with a procedure called total joint arthroplasty (TJR). TJR is an orthopedic surgical procedure in which the (typically) worn articular surfaces of the joint are replaced with prosthetic components, or implants. TJR typically requires the removal of the articular cartilage of the joint including a varying amount of bone. This cartilage and bone is then replaced with synthetic implants, typically metal and plastic, which form the new synthetic joint surfaces.

The accurate placement and alignment of the implants on the bone is a large factor in determining the success of a TJR procedure. A slight misalignment may result in poor wear characteristics, reduced functionality, poor clinical outcomes, and decreased longevity. Therefore, several TJR procedures are now frequently performed with computer-assistance, and even more advanced procedures utilize robotic surgical systems. One such robotic surgical system is the TSOLUTION ONE® Surgical System (THINK Surgical, Inc., Fremont, CA) which aids in the planning and execution of total hip arthroplasty (THA) and total knee arthroplasty (TKA). The TSOLUTION ONE® Surgical System includes: (i) a pre-operative planning software program to generate a surgical plan using an image data set and/or 3-D models of the patient's bone and computer-aided design (CAD) models of various implants; and (ii) an autonomous surgical robot that precisely mills the bone to receive an implant according to the surgical plan.

With reference to FIG. 1, an end-effector 10 having a cutter 12 is shown cutting a cavity C in a bone B. During robotic cutting, the forces experienced on the end-effector 10 are monitored with a force sensor 14 for patient safety. If the measured forces exceed a threshold force, the robot arm manipulating the end-effector 10 is immediately frozen to allow the user (e.g., a surgeon) to inspect the surgical site and ensure that the robot is cutting as intended. In some instances, the cutter 12 may have encountered dense cortical bone that may be difficult to cut with the current operating parameters (e.g., spindle speed and feed rate). In other instances, a non-cutting portion of the end-effector, such as a sleeve 16 that surrounds and supports a cantilevered cutter 12, may have inadvertently contacted another portion of the bone, or another object, which might impede the cutter's cut path. In either situation, the procedure is paused to adjust the operating parameters or the position of the bone (or other object) before the cutting is resumed.

In addition, the motion of the bone is monitored during robotic cutting to ensure the cuts are created in the planned positions. By way of example but not limitation, the position of the bone may be monitored by one or more strain-gauges attached to the bone (see below), or by a tracking marker attached to the bone that is tracked by a tracking system (see below), etc. If the bone moves a threshold distance, the robot arm is "frozen" (i.e., stopped) to permit a user (e.g., a surgeon) to assess and fix (i.e., resolve) the situation before the cutting is resumed.

The above safety mechanisms are critical for patient safety and the success of the surgical procedure. However, once the robot arm is frozen (i.e., stopped), the additional time needed to assess and fix the situation affects the overall operating time, which is ideally kept to a minimum. In extreme circumstances, the robotic procedure may need to be aborted. Currently, the user (e.g., a surgeon) has limited or no access to information regarding the cutting forces and/or bone motions occurring during cutting, which could otherwise help the user (e.g., a surgeon) to act before excessive forces or bone motions are encountered.

Thus there exists a need in the art for a system and method to provide bone motion and cutting force feedback to the user (e.g., a surgeon) during robotic surgery in order to improve robotic cutting and reduce operating times.

SUMMARY OF THE INVENTION

The present invention comprises the provision and use of a novel system and method to provide bone motion and cutting force feedback to the user (e.g., a surgeon) during robotic surgery in order to improve robotic cutting and reduce operating times.

In one preferred form of the invention, there is provided a method for using cutting force and/or bone motion feedback during robotic surgery to improve robotic cutting and reduce operating time, the method comprising:
  acquiring at least one of cutting force data and bone motion data during robotic cutting;
  displaying an indication of at least one of the cutting force data and the bone motion data to a user in real-time;
  pausing the robotic cutting in response to an indication signaling at least one of the following problematic conditions:
    a cutting force magnitude exceeding a threshold force;
    an off-axis cutting force vector exceeding a threshold angle from an expected cutting force vector;
    a positional or time derivative of a cutting force magnitude exceeding a threshold force;
    a positional or time derivative of an off-axis cutting force vector exceeding a threshold value;
    a bone motion magnitude exceeding a threshold magnitude;
    an off-axis bone motion vector exceeding a threshold angle from an expected bone motion vector;
    a positional or time derivative of a bone motion magnitude exceeding a threshold magnitude; and
    a positional or time derivative of an off-axis bone motion vector exceeding a threshold value; and mitigating the at least one problematic condition by adjusting at least one of (i) one or more cutting parameters, and (ii) a position of a bone prior to resuming the robotic cutting.

In another preferred form of the invention, there is provided a method for improved robotic cutting, the method comprising:

determining at least one of cutting force data and bone motion data during robotic cutting;

determining when at least one of the cutting force data and bone motion data exceeds a predetermined parameter; and when it is determined that at least one of the cutting force data and the bone motion data exceeds the predetermined parameter, providing the user with an indication of the same and pausing the robotic cutting so as to enable the user to mitigate the cause of at least one of the cutting force data and the bone motion data exceeding the predetermined parameter.

In another preferred form of the invention, there is provided apparatus for improved robotic cutting, the apparatus comprising:

a first unit for determining at least one of cutting force data and bone motion data during robotic cutting;

a second unit for determining when at least one of the cutting force data and bone motion data exceeds a predetermined parameter;

a third unit for, when it is determined that at least one of the cutting force data and the bone motion data exceeds the predetermined parameter, providing the user with an indication of the same and pausing the robotic cutting so as to enable the user to mitigate the cause of at least one of the cutting force data and the bone motion data exceeding the predetermined parameter.

BRIEF DESCRIPTION OF THE DRAWINGS

The present invention is further detailed with respect to the following drawings that are intended to show certain aspects of the present of invention, but should not be construed as limiting the present invention, wherein.

DETAILED DESCRIPTION

Figure 1:
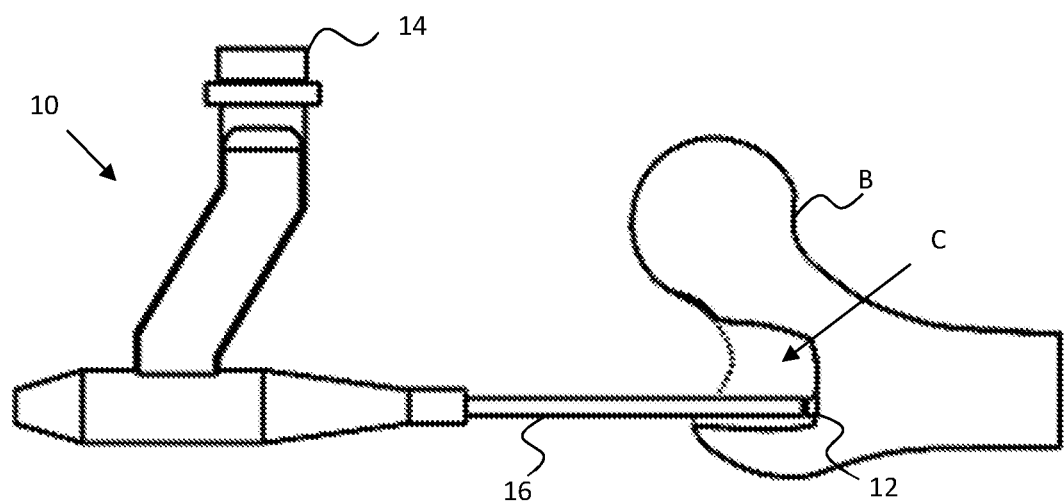
FIG. 1 is a schematic view showing the end-effector of a surgical robot cutting a cavity in a bone.

The present invention has utility as a system and method to provide bone motion and cutting force feedback to the user (e.g., a surgeon) during robotic surgery to improve robotic cutting and reduce operating time. The present invention will now be described with reference to the following embodiments. As is apparent by these descriptions, and as will be appreciated by those skilled in the art, this invention can be embodied in different forms and should not be construed as limited to the embodiments set forth herein. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure. Hence, the following specification is intended to illustrate some particular embodiments of the invention, and not to exhaustively specify all permutations, combinations, and variations thereof.

Further, it should be appreciated that although the systems and methods described herein may make reference to or show the proximal femur (e.g., in connection with hip arthroplasty), the systems and methods may be applied to other bones and joints in the body, including but not limited to other portions of the hip, the ankle, the elbow, the wrist, the skull, the spine, etc. as well as revisions of initial repairs or replacements of any of the aforementioned bones or joints.

As used herein, the term "pre-operative bone data" refers to bone data used to pre-operatively plan a procedure before making modifications to the actual bone. The pre-operative bone data may include one or more of the following: an image data set of a bone (e.g., acquired via computed tomography (CT), magnetic resonance imaging (MRI), ultrasound, x-ray, laser scan, etc.), a virtual generic bone model, a physical bone model, a virtual patient-specific bone model generated from an image data set of a bone, a set of data collected directly on a bone intra-operatively (commonly used with imageless computer-assist devices), etc.

As used herein, the term "registration" refers to the determination of the position and orientation (POSE) and/or coordinate transformation between two or more objects or coordinate systems such as a computer-assist device, a bone, pre-operative bone data, surgical planning data (e.g., an implant model, a computer software "cut-file" to identify a cutting path, virtual boundaries, virtual planes, cutting parameters associated with or defined relative to the pre-operative bone data, etc.), and any external landmarks (e.g., a fiducial marker array, an anatomical landmark, etc.) associated with the bone, if such landmarks exist. Various methods of registration are well known in the art and are described in, for example, U.S. Pat. Nos. 6,033,415, 8,010,177, and 8,287,522, which patents are hereby incorporated herein by reference.

As used herein, the term "real-time" refers to the processing of input data within milliseconds such that calculated values are available within 2 seconds of computational initiation.

Also described herein are "robotic surgical devices". A robotic surgical device refers to any device (or system) requiring computer control of an end-effector to aid in a surgical procedure. Examples of a robotic surgical device include active and haptic, 1 to N degree(s) of freedom (DOF) hand-held surgical devices and systems, autonomous serial-chain manipulator systems, haptic serial chain manipulator systems, parallel robotic systems, master-slave robotic systems, etc., as described in, for example, U.S. Pat. Nos. 5,086,401, 7,206,626, 8,876,830, and 8,961,536, U.S. Pat. Pub. No. 2013/0060278, and U.S. patent application Ser. No. 15/778,811, which patents, patent publications and

Figure 2:
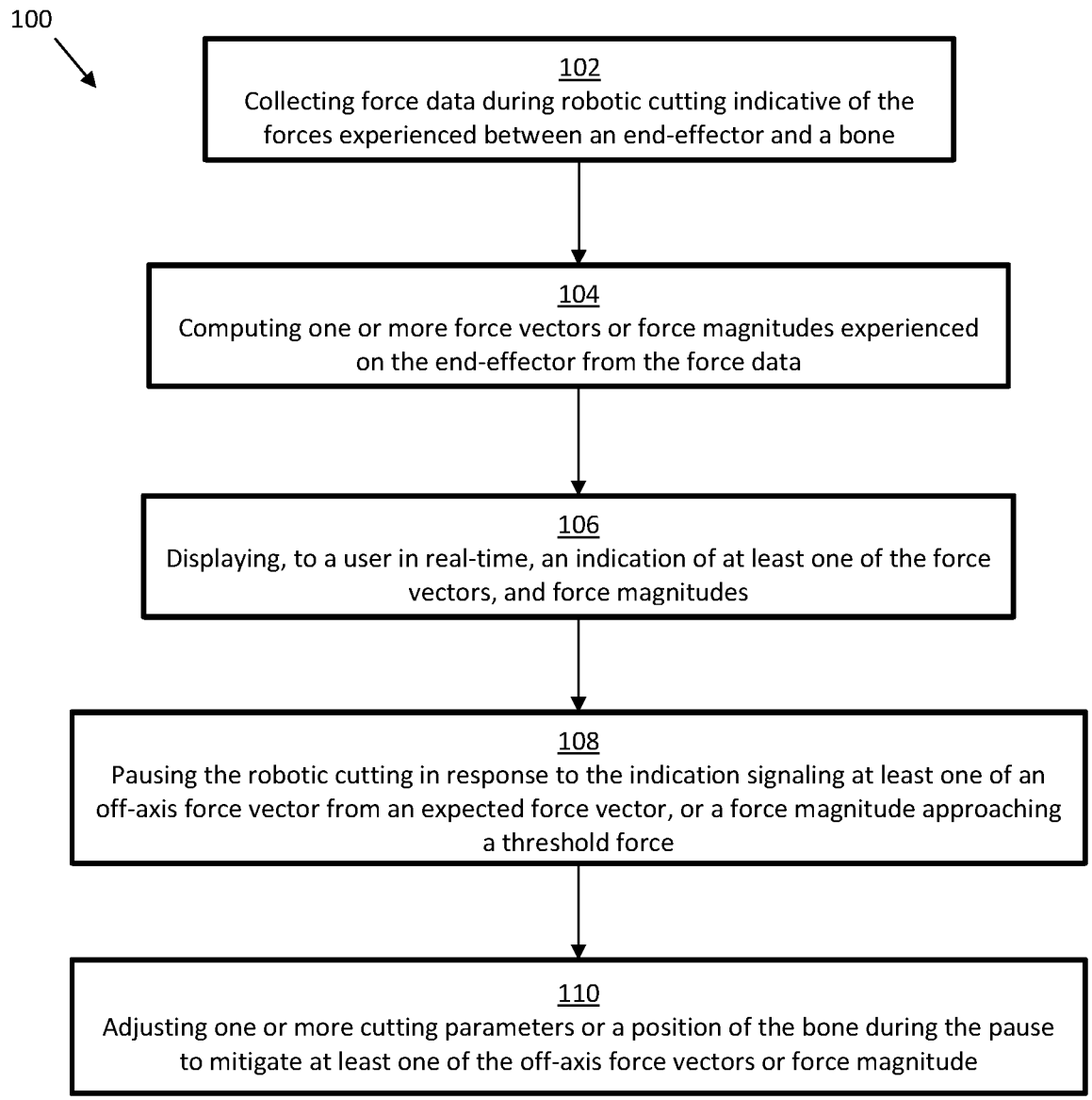
FIG. 2 is a flow diagram showing a novel method for providing cutting force feedback to a user (e.g., a surgeon) during robotic surgery to improve robotic cutting.

Method for Providing Cutting Force Feedback to a User (e.g., a Surgeon) During Robotic Surgery to Improve Robotic Cutting With reference now to the drawings, FIG. 2 depicts an embodiment of a method 100 to provide cutting force feedback to the user (e.g., a surgeon) during robotic surgery in order to improve robotic cutting and reduce operating time. The method 100 includes the following steps. Force data is collected during robotic cutting [Block 102]. The force data is indicative of the forces experienced between an end-effector 10 of the robot and the bone. The force data may be in various forms including: (i) force data collected from a force sensor 14, (ii) force data collected based on the electrical current requirements of the cutter, and/or (iii) force data based on audio data indicative of the spindle speed. One or more force vectors and/or force magnitudes is calculated based on the force data [Block 104]. An indication of the one or more force vectors and/or force magnitudes is displayed to the user (e.g., a surgeon) in real-time [Block 106]. The indication of the one or more force vectors and/or force magnitudes may be displayed to the user (e.g., a surgeon) with various indication mechanisms (e.g., as alpha-numerics or symbols or graphics displayed to a user (e.g., a surgeon) on a computer monitor) as further described below with reference to FIG. 5. If the force data indicates at least one of an "off-axis" force vector varying from an expected force vector, or a force magnitude approaching a threshold force magnitude, then the robotic cutting is paused by the user (e.g., a surgeon) to allow the user (e.g., a surgeon) to assess the situation [Block 108]. If needed, the user (e.g., a surgeon) can adjust one or more cutting parameters and/or a position of the bone during the pause in order to mitigate the problem associated with at least one of the off-axis force vectors or force magnitudes [Block 110].

Details of the embodiments of the method 100 are further described below.

As mentioned above, the force data may be collected from (i) a force sensor 14 (FIG. 1) monitoring the forces on the end-effector 10 during cutting, (ii) the electrical current requirements of the cutter, and/or (iii) audio data indicative of the spindle speed. The force sensor 14 may be a 6 degree-of-freedom (DOF) force sensor that measures both translational and rotational forces experienced by the end-effector 10. The force data from the force sensor 14 is sent to a computer for analysis in real-time. Another force feedback mechanism is the monitoring of the electrical current supplied to the cutter 12. The electrical current drawn by cutter 12 correlates to the power requirements needed by the cutter 12 to cut the bone at a particular region. In general, higher electrical currents indicate greater forces on the cutter 12 as more current is needed to cut the bony region. A third force feedback mechanism is the use of audio data that is a function of the spindle speed of the cutter 12. The audio feedback mechanism is further described below with reference to FIG. 4.

The force data acquired from the cutting operation is sent to a computer for analysis in real-time. From the force data acquired during cutting, one or more force vectors and/or force magnitudes is calculated. Where the force data is acquired from a 6-DOF force sensor 14, the force vector(s) or force magnitude(s) may be a direct output of the force sensor 14. In a particular embodiment, the computer applies a noise filter to the force data to more accurately compute the force vectors and/or force magnitudes. In some embodiments, the positional or time derivative of the force vectors or force magnitudes are calculated by the computer to determine the rate at which the force vectors or force magnitudes are changing, which is particularly advantageous in detecting a potential problem (e.g., force freeze) before the problem occurs. Under normal operating conditions, the force vector will correlate with the path of the cutter 12 (as determined by the surgical plan and kinematics of the robot), and the force magnitude will stay below a specified threshold. Where the force data is acquired by monitoring the electrical current drawn by the cutter 12, the electrical current may be monitored by a computer. As discussed above, the electrical current can provide an indication of the force magnitude experienced on the cutter 12. In some embodiments, a mathematical model is generated correlating the electrical current drawn by the cutter to the forces experienced by the cutter based on empirical data. This may provide an absolute value of the forces experienced between the cutter 12 and the bone B.

Figure 5:
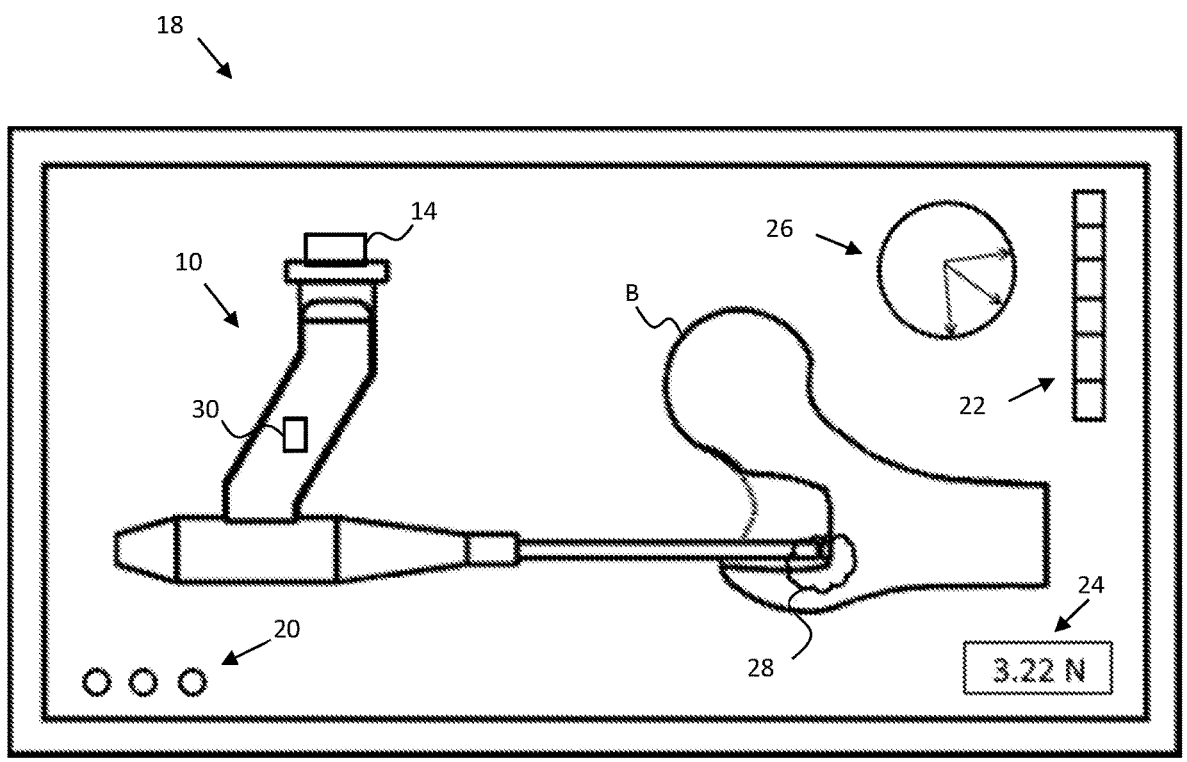
FIG. 5 is a schematic view showing indication mechanisms displayed on a monitor for providing bone motion and cutting force feedback to a user (e.g., a surgeon) during robotic surgery to improve robotic cutting.

The computer may then provide the user (e.g., a surgeon) with an indication, in real-time, of at least one of the force vector(s) and/or the force magnitude(s) experienced by the cutter. With reference to FIG. 5, a display monitor 18 is shown displaying the end-effector 10 cutting the bone B and several indication mechanisms to display the force data (e.g., force vectors and/or force magnitudes), and/or bone motion (see below). The indication mechanism presented on the display monitor 18 may include: one or more flashing lights 20, a magnitude meter 22, an alpha-numeric display 24, a vector display 26, and/or a cloud display 28. The indication mechanisms (which may also include light emitting diodes (LEDs)) may also be present on other devices including, but not limited to, a display located on a pendant (i.e., a control box for controlling a robot) or other hand-held controller, a digitizer, a tracking system housing, a tracking array, etc. In another embodiment, the indication of at least one of the force data and bone motion data may be displayed to a user using a light mounted to a device performing the robotic cutting.

The one or more flashing lights 20 may emit a color or frequency indicating at least one of the computed force vectors, force magnitudes, or the time or positional derivatives thereof. For example, the lights 20 may flash green when the vector is as expected (i.e., when the vector extends in the direction of the cutter's path) or when the force magnitude is below a threshold force. The lights 20 may turn yellow as the vector approaches a threshold angle deviating from the cutter's path, or the magnitude is approaching the threshold force. In particular situations, an off-axis force vector (i.e., a deviation from the planned cutter path) may occur when the sleeve 16 or another portion of a cantilever cutter 12 contacts another non-cutting portion of the bone B or another object. The lights 20 may also flash yellow when the derivatives of the force vectors or force magnitudes reach a specified value to indicate an increasing rate of change thereof. Alternatively and/or additionally, flashing lights 20 may modulate the flashing frequency of the light where, for example, the light flashes faster when the force vectors are off-axis, and/or when the force magnitudes are approaching a threshold, and/or the derivatives thereof reach a threshold. In this example, a yellow color or a specific flashing frequency may cause the user (e.g., a surgeon) to pause the procedure to assess the situation. It should be appreciated that the indication mechanisms may comprise other colors (e.g., red).

The magnitude meter 22 may function similar to an "audio level" meter, which displays a bar having a height corresponding to the force magnitude (e.g., a taller bar reflects a greater force, a shorter bar reflects a lesser force). If the height of the bar approaches a level indicating that the force magnitude approaching a force threshold, the user (e.g., a surgeon) may pause the procedure to assess the situation.

The alpha-numeric display 24 may directly display an indication of the force vector, force magnitude, or the position/time derivatives thereof. For example, the alpha-numeric display 24 may display the magnitude of the force, or an angle of off-set between the cutter's path and the calculated force vector, etc.

The vector display 26 may display the calculated force vectors. The vector display 26 may also display the vector of the cutter's path for reference, so that the user (e.g., a surgeon) can monitor any off-set between the two.

The cloud display 28 may display a cloud around the expected force origin. Here, the expected force origin is the location of the cutting occurring between the cutter 12 and the bone B. The cloud 28 may change in size and/or shape and/or position to indicate a magnitude of the force or the presence of an off-axis force. For example, the cloud may increase in size to indicate the magnitude of the force, and/or change in shape, and/or change in position (e.g., proximally or distally relative to cutter 12, and/or to one side or the other of cutter 12) if a calculated off-axis vector is approaching a threshold angle. Furthermore, cloud 28 may change in color if the magnitude of the force is approaching a threshold level, or cloud 28 may change in color if a calculated off-axis vector is approaching a threshold angle. Note that cloud display 28 may also be used to indicate bone motion (see below).

In some embodiments, the indication mechanisms may display an indication of the raw force data, or the electrical current drawn by the cutter, where the user has a reference or benchmark number to ascertain if one or more problems may occur.

Based on any of the above indications, the user (e.g., a surgeon) may pause the procedure when the indication mechanism signals at least one of the following problems: a force magnitude approaching or exceeding a threshold force; an off-axis force vector approaching or exceeding a threshold angle from an expected force vector; or the positional or time derivative of the force magnitude or off-axis force vector approaching a threshold. During the pause, the user (e.g., a surgeon) can assess the situation to mitigate the problems prior to resuming the robotic cutting. The user (e.g., a surgeon) may change the cutting operating parameters (e.g., spindle speed, feed rate, replace a wearing cutter if needed, adjust a cut-path, etc.), and/or adjust the position of the bone or robot, to improve the orientation of the robot arm into a more favorable cutting orientation. Thus, more severe problems or issues are mitigated to improve robotic cutting and reduce the overall operating time.

Figure 3:
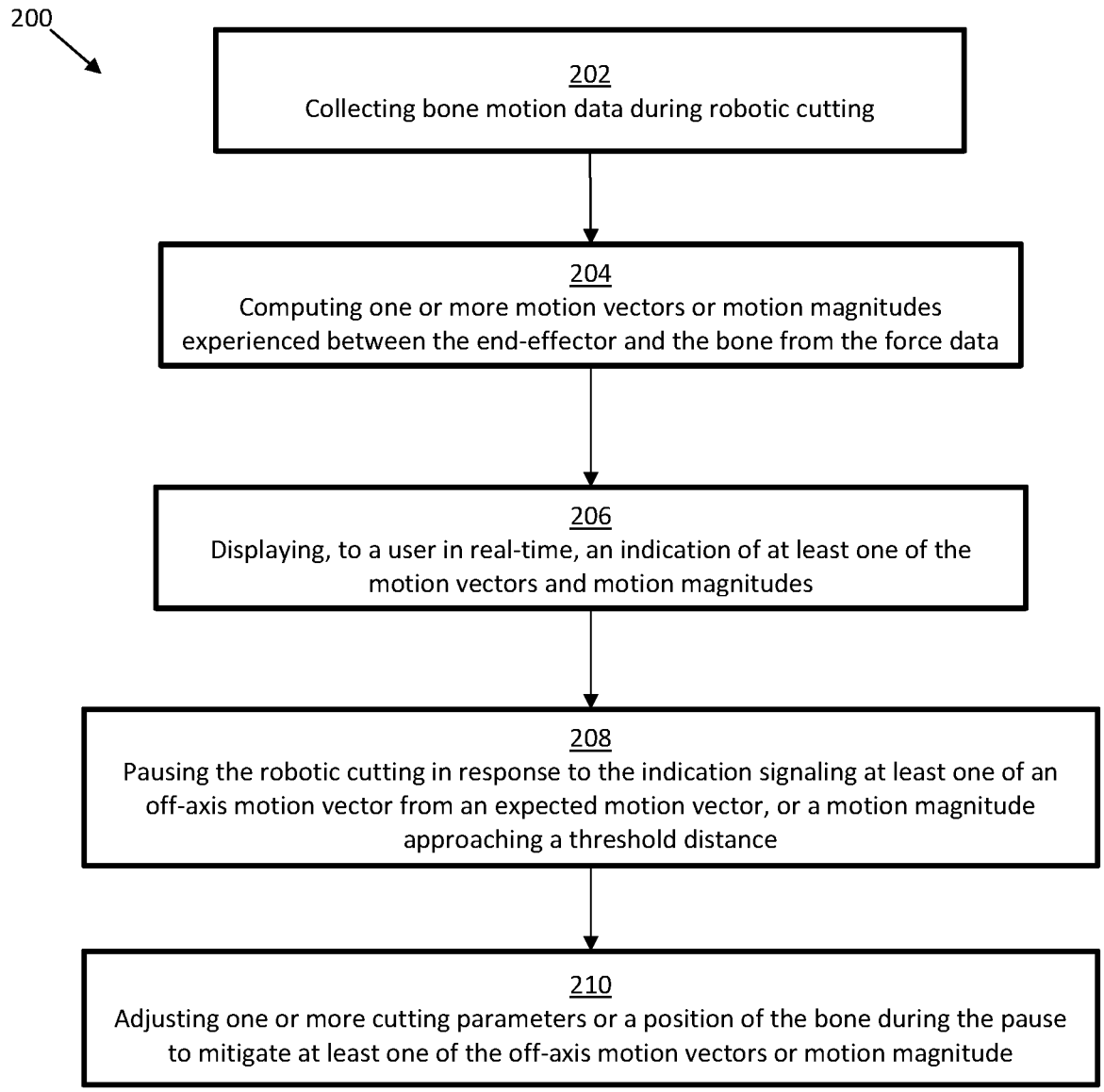
FIG. 3 is a flow diagram showing a novel method for providing bone motion feedback to a user (e.g., a surgeon) during robotic surgery to improve robotic cutting.

Method for Providing Bone Motion Feedback to a User (e.g., a Surgeon) During Robotic Surgery to Improve Robotic Cutting With reference to FIG. 3, a particular embodiment of a method 200 to provide bone motion feedback to the user (e.g., a surgeon) during robotic surgery to improve robotic cutting and reduce operating time is shown. The method includes the following steps. Bone motion data is collected during robotic cutting [Block 202]. One or more bone motion vectors and/or bone motion magnitudes between the end-effector 10 and the bone B is computed [Block 204]. An indication of the one or more bone motion vectors and/or bone motion magnitudes is displayed to the user in real-time [Block 206]. The indication may be displayed to the user (e.g., a surgeon) with the aforementioned indication mechanisms (e.g., on a display monitor) discussed above with respect to method 100, e.g., one or more flashing lights 20, a magnitude meter 22, an alpha-numeric display 24, a vector display 26, and/or a cloud display 28. If the indication signals at least one of an "off-axis" motion vector varying from an expected motion vector, or a bone motion magnitude approaching a threshold bone motion magnitude, then the robotic cutting is paused by the user (e.g., a surgeon) to allow the user (e.g., a surgeon) to assess the situation [Block 208]. If needed, the user (e.g., a surgeon) can adjust one or more cutting parameters or a position of the bone during the pause in order to mitigate the problem associated with at least one of the off-axis bone motion vectors or bone motion magnitudes [Block 210].

Details of the embodiments of the method 200 are further described below.

Bone motion data may be collected with the use of one or more strain-gauges attached to the bone, or a tracking marker attached to the bone that is tracked by a tracking system. Examples of bone motion tracking are described in U.S. Pat. No. 6,322,567 which is hereby incorporated by reference herein in its entirety.

The bone motion data acquired from the cutting operation is sent to a computer for analysis in real-time. From the bone motion data, one or more bone motion vectors and/or bone motion magnitudes is calculated. In a particular embodiment, the computer applies a noise filter to the bone motion data to more accurately compute the bone motion vectors and/or bone motion magnitudes. In some embodiments, the positional or time derivative of the bone motion vectors or bone motion magnitudes are calculated by the computer to determine the rate at which the bone motion vectors or bone motion magnitudes are changing, which is particularly advantageous in detecting a potential problem (e.g., force freeze) before the problem occurs. Under normal operating conditions, the bone motion vector will correlate with the path of the cutter 12, and the bone motion magnitude will stay below a specified threshold (e.g., less than 2 mm for no more than 2 seconds).

The computer may then provide the user (e.g., a surgeon) with an indication, in real-time, of at least one of the bone motion vector(s) and/or bone motion magnitudes. Any of the aforementioned indication mechanisms discussed above with respect to method 100 may be used to display this data (e.g., on display monitor 18), e.g., one or more flashing lights 20, a magnitude meter 22, an alpha-numeric display 24, a vector display 26, and/or a cloud display 28. Based on the indication (i.e., the data displayed), the user (e.g., a surgeon) can respond as above to assess the situation and mitigate any problems.

Figure 4:
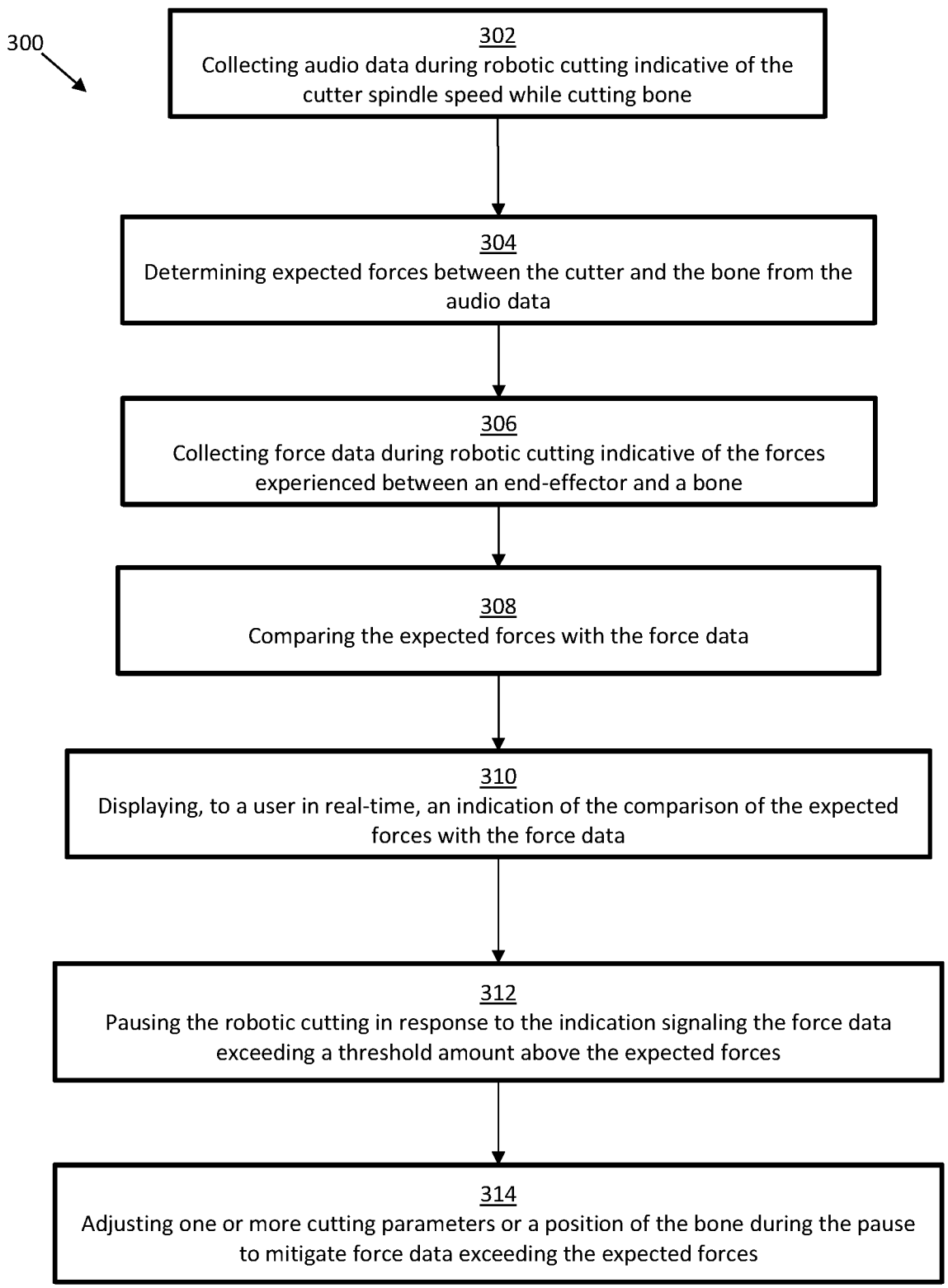
FIG. 4 is a flow diagram showing a novel method for using audio monitoring to provide cutting force feedback to a user (e.g., a surgeon) during robotic surgery to improve robotic cutting.

Method for Using Audio Monitoring to Provide Cutting Force Feedback to a User (e.g., a Surgeon) During Robotic Surgery to Improve Robotic Cutting With reference to FIG. 4, a specific embodiment of a method 300 utilizing audio monitoring to provide feedback during robotic surgery to improve robotic cutting and reduce operating time is shown. The method 300 includes the following steps. Audio data is collected during robotic cutting indicative of the cutter spindle speed while cutting bone [Block 302]. The expected forces between the cutter 12 and the bone B is determined based on the audio data [Block 304]. Force data is also collected during robotic cutting indicative of the forces experienced between the end-effector 10 and the bone B [Block 306]. The expected forces are compared to the force data [Block 308]. An indication of the comparison between the expected forces and force data is displayed to the user (e.g., a surgeon) in real-time [Block 310]. The robotic cutting may be paused in response to an indication signaling that the force data exceeds the expected forces by a threshold amount [Block 312]. If needed, the user (e.g., a surgeon) may adjust one or more cutting parameters or a position of the bone during the pause to mitigate the force data exceeding the expected forces by the threshold amount [Block 314].

Details of specific embodiments of the method 300 are described below.

Figure 6:
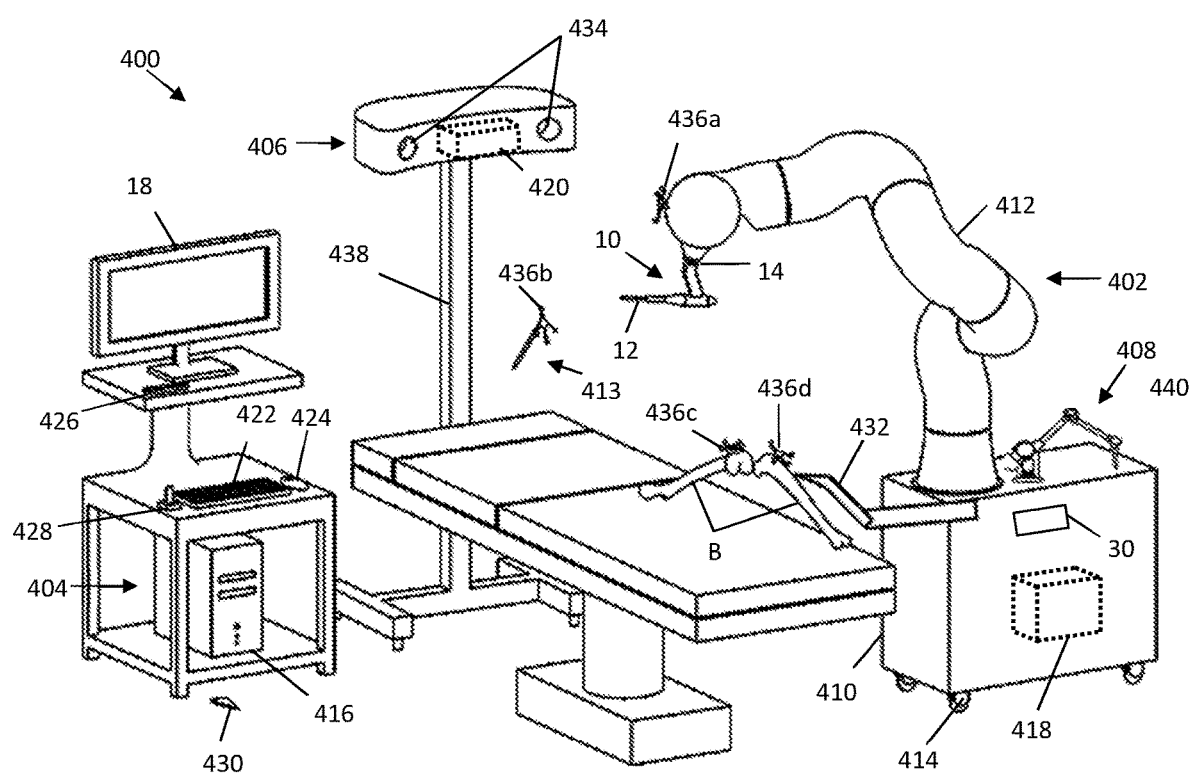
FIG. 6 is a schematic view showing a robotic surgical system incorporating the present invention.

An audio sensor 30 in communication with a computer is present in the operating room "OR" (e.g., on the end-effector 10 as shown in FIG. 5, on the robot as shown in FIG. 6, or elsewhere in the OR) to detect audio data of the cutter 12 during cutting. Audio data can be correlated to the spindle speed of the cutter 10 and may further be correlated to the spindle speed of the cutter 10 cutting of particular types of bone B. For example, a particular audio frequency may be correlated with a particular spindle speed and/or a particular spindle speed cutting a particular type of bone B (e.g., trabecular, cortical, and densities therebetween). A mathematical model may be generated to further correlate these audio frequencies with force data using empirical data. For example, several cadaver bones may be cut with the cutter 12 for a variety of surgical plans. While cutting the cadaver bones, acoustic data and force data are collected with the audio sensor 30 and a force sensor 14, respectively. The acoustic data, force data, and the cutting parameters (e.g., spindle speed, feed rate) are then used to build the mathematical model to correlate these variables, thus providing a relationship between the audio data and the expected forces between the cutter 12 and the bone B. In the operating room, while cutting the patient's actual bone, the model may be used to determine the expected forces from the collected audio data.

As the audio data is collected, force data is collected at the same time. The force data may be collected with a force sensor 14 or based on the electrical current requirements of the cutter 12. The expected forces determined from the acoustic data is then compared to the force data. Under normal operating conditions, the expected forces (from the acoustic data) and the force data are within statistical agreement. If the force data is higher than the expected forces (statistically higher or above a specified threshold), then there is a strong possibility that another part of the cantilevered cutter 12 or the sleeve 16 is contacting a non-cutting portion of the bone B, which may cause a force freeze or affect patient safety. To mitigate this problem, an indication of the acoustic data, the expected forces, the force data, or a comparison therebetween is displayed to the user (e.g., a surgeon) in real-time. Any of the aforementioned indication mechanisms may be used to display the indication (i.e., of the acoustic data, the expected forces, the force data, or a comparison therebetween), or to display the raw data directly (e.g., on display monitor 18), e.g., one or more flashing lights 20, a magnitude meter 22, an alpha-numeric display 24, a vector display 26, and/or a cloud display 28. If the indication signals that the force data is above the expected forces, the robotic cutting may be paused to assess the situation. If needed, the user (e.g., a surgeon) can adjust one or more cutting parameters or a position of the bone during the pause to mitigate the force data exceeding the expected forces.

Robotic Surgical System

With reference to FIG. 6, an embodiment of a robotic surgical system 400 is shown capable of implementing embodiments of the inventive method described above. The aforementioned devices and methods are particularly useful for a robotic surgical system 400, which traditionally experiences longer surgical times compared to manual techniques or techniques using hand-held tracked instrumentation.

The surgical system 400 generally includes a surgical robot 402, a computing system 404, and a tracking system 406 and/or a mechanical digitizer 408.

The surgical robot 402 may include a movable base 410, a manipulator arm 412 connected to the base 410, an end-effector 10 located at a distal end of the manipulator arm 412, and a force sensor 14 positioned proximal to the end-effector 10 for sensing forces experienced by the end-effector 10. The base 410 includes a set of wheels 414 to maneuver the base 410, which may be fixed into position using a braking mechanism such as a hydraulic brake. The base 410 may further include an actuator to adjust the height of the manipulator arm 412. The manipulator arm 412 includes various joints and links to manipulate the end-effector 10 in various degrees of freedom. The joints are, illustratively, prismatic, revolute, spherical, or a combination thereof. In some embodiments, the surgical system 400 includes at least one of a tracked digitizer 413 or a mechanical digitizer arm 408 attached to the base 410. The tracked digitizer 413 may include a tracking array 436b to be tracked by the tracking system 406, while the digitizer arm 408 may have its own tracking computer or may be directly connected with the device computer 418 (i.e., the device computer for surgical robot 402).

The computing system 404 generally includes a planning computer 416; the device computer 418; a tracking computer 420; and peripheral devices (see below). The planning computer 416, device computer 418, and tracking computer 420 may be separate entities, one-in-the-same, or combinations thereof, depending on the surgical system. Further, in some embodiments, a combination of the planning computer 416, the device computer 418, and/or tracking computer 420 are connected to one another via a wired or wireless communication. The peripheral devices (mentioned above) allow a user to interface with the surgical system components and may include: one or more user-interfaces, such as the aforementioned display monitor 18 (which is also used to display the aforementioned indication mechanisms, e.g., one or more flashing lights 20, a magnitude meter 22, an alpha-numeric display 24, a vector display 26, and/or a cloud display 28) for the graphical user interface (GUI); and user-input mechanisms, such as a keyboard 422, mouse 424, pendent 426, joystick 428, foot pedal 430, or the monitor 18 in some embodiments has touchscreen capabilities.

The planning computer 416 contains hardware (e.g., processors, controllers, and/or memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan may include pre-operative bone data, patient data, registration data including the POSE of the points P defined relative to the pre-operative bone data, implant position data, trajectory parameters, and/or operational data. The operational data may include: a set of instructions for modifying a volume of tissue that is defined relative to the anatomy, such as a set of cutting parameters (e.g., cut paths, spindle-speeds, feedrates) in a cut-file to autonomously modify the volume of bone; a set of virtual boundaries defined to haptically constrain a tool within the defined boundaries to modify the bone; or a set of planes or drill holes to drill pins in the bone. In particular inventive embodiments, the operational data specifically includes a cut-file for execution by a surgical robot to autonomously modify the volume of bone, which is advantageous from an accuracy and usability perspective. The surgical plan data provided by the planning computer 416 may be transferred to the device computer 418 and/or tracking computer 420 through a wired or wireless connection in the operating room (OR); or transferred via a non-transient data storage medium (e.g., a compact disc (CD), a portable universal serial bus (USB) drive) if the planning computer 416 is located outside the OR. In some embodiments, the surgical plan is transferred via visible light communication such as is described in U.S. Pat. Pub. No. 20170245945 assigned to the assignee of the present application, which patent application is hereby incorporated herein by reference.

The device computer 418 in some inventive embodiments is housed in the moveable base 410 and contains hardware, software, data and utilities that are preferably dedicated to the operation of the surgical robot 402. This may include surgical device control, robotic manipulator control, the processing of kinematic and inverse kinematic data, the execution of registration algorithms, the execution of calibration routines, the execution of operational data (e.g., cut-files, the trajectory parameters), coordinate transformation processing, providing workflow instructions to a user (e.g., a surgeon), and utilizing position and orientation (POSE) data from the tracking system 406. The device computer 418 may further be in communication with the force sensor 14, audio sensor 30, or a plurality of strain gauges 432 attached to the bone, to compute at least one of the: force vectors, force magnitudes, bone motion vectors, bone motion magnitudes, or expected forces from the audio data as described above. In addition, the device computer 418 is in communication with the display monitor 18 (which displays the aforementioned indication mechanisms, e.g., one or more flashing lights 20, a magnitude meter 22, an alpha-numeric display 24, a vector display 26, and/or a cloud display 28) to provide the instructions to display the aforementioned indications as they relate to the various embodiments of the methods (100, 200, and 300) described above.

The tracking system 406 may be an optical tracking system that includes two or more optical receivers 434 to detect the position of fiducial markers (e.g., retroreflective spheres, active light emitting diodes (LEDs)) uniquely arranged on rigid bodies. The fiducial markers arranged on a rigid body are collectively referred to as a tracking array (436a, 436b, 436c, 436d), where each fiducial marker array 436 has a unique arrangement of fiducial markers, or a unique transmitting wavelength/frequency if the markers are active LEDs. The fiducial markers may likewise be integrated or attached with a device directly to act as a tracking array for that device. An example of an optical tracking system is described in U.S. Pat. No. 6,061,644, which patent is hereby incorporated herein by reference. The tracking system 406 may be built into a surgical light, located on a boom attached to a stand 438, or built into the walls or ceilings of the OR. The tracking system computer 420 may include tracking hardware, software, data and utilities to determine the POSE of objects (e.g., bones B, surgical robot 402) in a local or global coordinate frame. The POSE of the objects is collectively referred to herein as POSE data, where this POSE data may be communicated to the device computer 418 through a wired or wireless connection. Alternatively, the device computer 418 may determine the POSE data using the position of the fiducial markers detected from the optical receivers 434 directly.

The POSE data is determined using the position data detected from the optical receivers 434 and operations/processes such as image processing, image filtering, triangulation algorithms, geometric relationship processing, registration algorithms, calibration algorithms, and coordinate transformation processing.

The POSE data is used by the computing system 404 during the procedure to update the POSE and/or coordinate transforms of the bone B, the surgical plan, and the surgical robot 402 as the manipulator arm 412 and/or bone B move during the procedure, such that the surgical robot 402 can accurately execute the surgical plan. Data from the tracking system 406 may also be used to determine at least one of the bone motion vectors and/or bone motion magnitudes as described above. In some embodiments, the tracking system 406 is in communication with the display monitor 18 (which displays the aforementioned indication mechanisms, e.g., one or more flashing lights 20, a magnitude meter 22, an alpha-numeric display 24, a vector display 26, and/or a cloud display 28) to provide instructions to display the aforementioned indications as they relate to the various embodiments of the methods (100, 200, and 300) described above.

In another embodiment, the robotic surgical system 400 does not include an optical tracking system, but instead employs a mechanical arm 440 that acts as a tracking system as well as a mechanical digitizer 408 or a projecting digitizer. If the bone is not tracked, a bone fixation and bone monitoring system (e.g., strain gauges 432) may fix the bone directly to the surgical robot 402 to monitor bone movement as described in U.S. Pat. No. 5,086,401, which patent is hereby incorporated herein by reference.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:
1. A method for operating a surgical robot, the method comprising:

acquiring feedback data with two sensors during a bone cutting procedure using the surgical robot, wherein the feedback data comprises cutting force data and bone motion data;

displaying a real-time comparison of the feedback data to a predetermined parameter during the bone cutting procedure using the surgical robot, wherein the real-time comparison is displayed as a visual feature comprising a flashing light, wherein the flashing light changes a color or a flashing frequency depending on an extent to which the feedback data approaches the predetermined parameter; and receiving a computer input from a user of the surgical robot to control an operation of the surgical robot before the feedback data exceeds the predetermined parameter.

2. The method according to claim 1, wherein the real-time comparison is displayed on a monitor.

3. The method according to claim 2, wherein the real-time comparison is displayed as a visual feature comprising a magnitude meter, an alpha-numeric display, a vector display or a cloud display.

4. The method according to claim 3, wherein the visual feature comprises a magnitude meter comprising a bar, and wherein a height of the bar represents a magnitude of the feedback data.

5. The method according to claim 3, wherein the visual feature comprises a vector display comprising an arrow, wherein a direction of the arrow represents a direction of the feedback data, and wherein a length of the arrow represents a magnitude of the feedback data.

6. The method according to claim 3, wherein the visual feature comprises a cloud display, and wherein a size or color of the cloud display varies in accordance with the feedback data.

7. The method according to claim 1, wherein the real-time comparison is displayed with a light coupled to at least a portion of the surgical robot.

8. The method according to claim 1, further comprising adjusting at least one cutting parameter of the surgical robot in response to the computer input.

9. The method according to claim 8, wherein the surgical robot comprises a cutting device, and wherein the at least one cutting parameter comprises:
a spindle speed of the cutting device;
a feed rate of the cutting device; and
a cut path of the cutting device.

10. The method according to claim 9, wherein the feedback data is cutting force data, and the cutting force data is calculated using current supplied to the cutting device or audio data which is a function of the spindle speed of the cutting device.

11. The method according to claim 1, further comprising pausing the operation of the surgical robot in response to the computer input and adjusting a position of a bone or a position of the surgical robot prior to resuming the bone cutting procedure.

12. The method according to claim 1, wherein the feedback data is cutting force data and the predetermined parameter comprises:
a threshold magnitude of cutting force;
a threshold angle of an off-axis cutting force vector from an expected cutting force vector;
a threshold of a positional or time derivative of a cutting force magnitude; or
a threshold of a positional or time derivative of the off-axis cutting force vector.

13. The method according to claim 1, wherein the feedback data is bone motion data and the predetermined parameter comprises:
a threshold magnitude of bone motion;
a threshold angle of an off-axis bone motion vector from an expected bone motion vector;
a threshold of a positional or time derivative of a bone motion magnitude; or
a threshold of a positional or time derivative of the off-axis bone motion vector.

14. The method according claim 1, wherein the two sensors comprise a force sensor for acquiring the cutting force data.

15. The method according to claim 1, wherein the two sensors comprise a position sensor for acquiring the bone motion data, and wherein the position sensor comprises a mechanical digitizer, an optical tracker, or at least one strain-gauge.

16. The method according to claim 15, wherein the two sensors comprise the at least one strain-gauge attached to a bone.

17. The method according to claim 1, wherein the surgical robot is an autonomous surgical robot executing a cut-file with instructions to remove material from a bone.

18. The method according to claim 1, wherein the bone cutting procedure is a robotic orthopedic surgical procedure.

19. The method according to claim 1, wherein the control the operation of the surgical robot comprises (i) pausing operation of the surgical robot in response to the computer input or (ii) continuing operation of the surgical robot.

20. The method according to claim 1, wherein the feedback data is the bone motion data comprising bone motion vectors or magnitudes of bone motion which are computed between an end-effector of the surgical robot and a bone.

* * * * *